(12) United States Patent
Hwang et al.

(10) Patent No.: US 12,042,121 B2
(45) Date of Patent: Jul. 23, 2024

(54) MEDICAL SYSTEM WITH MEDICAL DEVICE OVERLAY DISPLAY

(71) Applicant: CANON U.S.A., INC., Melville, NY (US)

(72) Inventors: Charles George Hwang, Wellesley, MA (US); Takahisa Kato, Brookline, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 17/564,534

(22) Filed: Dec. 29, 2021

(65) Prior Publication Data

US 2022/0202274 A1 Jun. 30, 2022

Related U.S. Application Data

(60) Provisional application No. 63/131,485, filed on Dec. 29, 2020.

(51) Int. Cl.
*A61B 1/00* (2006.01)
*A61B 1/267* (2006.01)
(Continued)

(52) U.S. Cl.
CPC ........ *A61B 1/0005* (2013.01); *A61B 1/00055* (2013.01); *A61B 1/267* (2013.01); *A61B 5/0035* (2013.01); *A61B 5/055* (2013.01); *A61B 5/7425* (2013.01); *A61B 6/032* (2013.01); *A61B 6/463* (2013.01); *A61B 6/5247* (2013.01); *G06F 3/016* (2013.01); *G06F 3/14* (2013.01); *G06T 11/003* (2013.01); *G06T 2210/41* (2013.01)

(58) Field of Classification Search
CPC ... A61B 1/0005; A61B 1/00055; A61B 1/267; A61B 5/0035; A61B 5/055; A61B 5/7425; A61B 6/032; A61B 6/463; A61B 6/5247; G06F 3/016; G06F 3/14; G06F 3/147; G06T 11/003; G06T 2210/41; G09G 2340/12; G09G 2360/16; G09G 2380/08

See application file for complete search history.

(56) References Cited

U.S. PATENT DOCUMENTS 6,214,019 B1 * 4/2001 Manwaring ............ A61B 90/10
606/130
10,720,029 B1 * 7/2020 Mears .................. A61B 5/1176
(Continued)

FOREIGN PATENT DOCUMENTS

KR 20160051738 A 5/2016
WO 2018/204202 A1 11/2018
(Continued)

*Primary Examiner* — Sean D Mattson
(74) *Attorney, Agent, or Firm* — Canon U.S.A., Inc., IP Division

(57) ABSTRACT

A medical system including a medical device having an outer diameter, a display device, and a controller. The controller is configured to acquire data regarding a biological lumen such as an airway structure, acquire an image of the airway structure, generate an overlay representing the outer diameter of the medical device, and display, on the display device, the overlay representing the outer diameter of the medical device on the acquired image of the airway structure. The overlay is scaled relative to a diameter of the airway structure at a focal plane of the airway structure based on the acquired data.

17 Claims, 5 Drawing Sheets

(51) Int. Cl.
*A61B 5/00* (2006.01)
*A61B 5/055* (2006.01)
*A61B 6/00* (2024.01)
*A61B 6/03* (2006.01)
*A61B 6/46* (2024.01)
*G06F 3/01* (2006.01)
*G06F 3/14* (2006.01)
*G06T 11/00* (2006.01)

(56) References Cited

U.S. PATENT DOCUMENTS

| | | |
|---|---|---|
| 2012/0197086 A1* | 8/2012 | Morris ............... A61B 1/00045 600/188 |
| 2017/0340241 A1* | 11/2017 | Yamada ................. G16H 50/30 |
| 2018/0015256 A1* | 1/2018 | Southard ............. A61B 8/0841 |
| 2018/0206922 A1 | 7/2018 | Wenderow et al. |
| 2018/0243900 A1 | 8/2018 | Tanaka et al. |
| 2018/0311006 A1 | 11/2018 | Kose et al. |
| 2019/0015978 A1 | 1/2019 | Takagi et al. |
| 2019/0105468 A1 | 4/2019 | Kato et al. |
| 2019/0192131 A1* | 6/2019 | Bush, Jr. ............ A61B 17/0218 |
| 2020/0078103 A1* | 3/2020 | Duindam ................ A61B 34/25 |
| 2021/0244260 A1* | 8/2021 | Uyama .............. A61B 1/00048 |

FOREIGN PATENT DOCUMENTS

| | | |
|---|---|---|
| WO | 2020/086749 A1 | 4/2020 |
| WO | 2020/092096 A2 | 5/2020 |

* cited by examiner

MEDICAL SYSTEM WITH MEDICAL DEVICE OVERLAY DISPLAY

CROSS-REFERENCE TO RELATED APPLICATIONS

The present application claims priority to U.S. provisional application 63/131,485 filed Dec. 29, 2020. The disclosure of the above-listed provisional application is hereby incorporated by reference in its entirety for all purposes. Priority benefit is claimed under 35 U.S.C. § 119(e).

FIELD OF DISCLOSURE

The present disclosure relates generally to systems and methods for medical applications. More particularly, the subject disclosure is directed to a system using an articulated medical device, wherein the medical device is capable of maneuvering within a patient.

BACKGROUND OF THE DISCLOSURE

Bendable medical devices such as endoscopic surgical devices and catheters are well known and continue to gain acceptance in the medical field. The bendable medical device generally includes a flexible body commonly referred to as a sleeves or sheaths. One or more tool channels extend along (typically inside) the flexible body to allow access to a target located at a distal end of the body.

The medical device is intended to provide flexible access within a patient, with at least one curve or more leading to the intended target, while retaining torsional and longitudinal rigidity so that a clinical user can control the tool located at the distal end of the medical device by maneuvering the proximal end of the device.

The medical device may be implemented via a system, where the system includes both hardware and software that when used together allow the user to guide and observe the movement of the medical device through passageways within a patient. By way of example, United States patent publication number 2019/0105468, describes such a system for implementing an articulated medical device having a hollow cavity, where the device is capable of maneuvering within a patient, and allowing a medical tool to be guided through the hollow cavity for medical procedures, including endoscopes, cameras, and catheters. However, when navigating the articulated medical device by video, there is no feedback mechanism to convey to the user that the pathway in which the medical device is traveling is too small. Without such feedback, the user may be confused as to why the articulated medical device is having difficulty moving through the pathway.

Accordingly, there exists a need in the art for a medical system that includes a feedback mechanism to convey to the user that the pathway in which the medical device is traveling is too small.

SUMMARY

The subject disclosure provides a medical system comprising a medical device having an outer diameter, a display device; and a controller configured to: acquire data regarding an airway structure; acquire an image of the airway structure; generate an overlay representing the outer diameter of the medical device, wherein the overlay is scaled relative to a diameter of the airway structure at a focal plane of the airway structure based on the acquired data, and display, on the display device, the overlay representing the outer diameter of the medical device on the acquired image of the airway structure.

These and other objects, features, and advantages of the present disclosure will become apparent upon reading the following detailed description of exemplary embodiments of the present disclosure, when taken in conjunction with the appended drawings, and provided paragraphs.

BRIEF DESCRIPTION OF THE DRAWINGS

Further objects, features and advantages of the present invention will become apparent from the following detailed description when taken in conjunction with the accompanying figures showing illustrative embodiments of the present invention.

Figure 1:
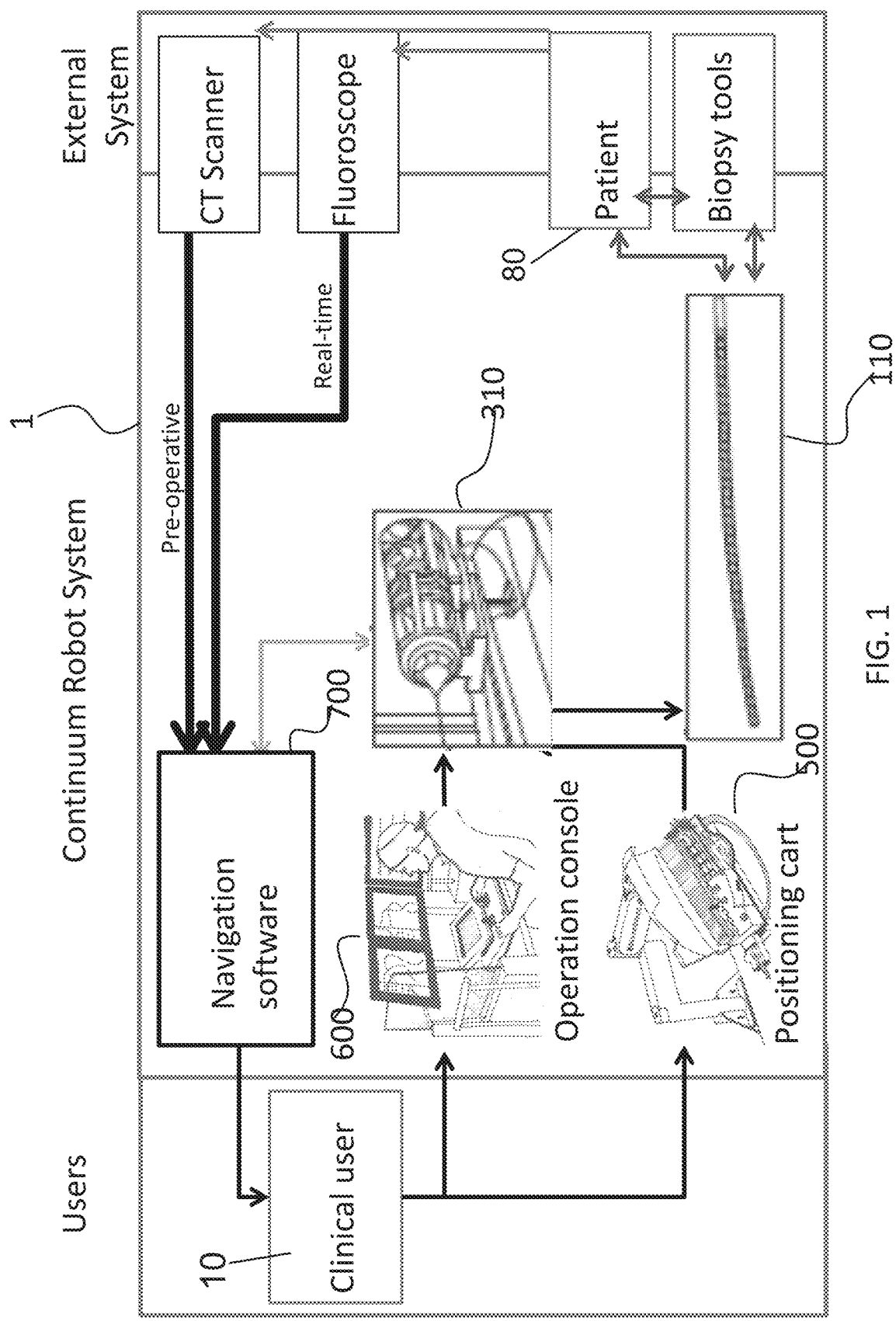
FIG. 1 illustrates an example embodiment of a system to allow a user to guide and observe the movement of a medical device within a patient.

Throughout the Figures, the same reference numerals and characters, unless otherwise stated, are used to denote like features, elements, components or portions of the illustrated embodiments. Moreover, while the subject disclosure will now be described in detail with reference to the Figures, it is done so in connection with the illustrative embodiments. It is intended that changes and modifications can be made to the described embodiments without departing from the true scope and spirit of the subject disclosure as defined by the appended paragraphs.

DETAILED DESCRIPTION

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

Unless specifically stated otherwise, as apparent from the following disclosure, it is understood that, throughout the disclosure, discussions using terms such as "processing," "computing," "calculating," "determining," "displaying," or the like, refer to the actions and processes of a processor such as a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computational or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic site. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade polymer material and having an optical imaging function. A particular example of an optical catheter is a fiber optic catheter which comprises a flexible sheath, a coil, and an optical probe or imaging core contained within the coil. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes. Embodiments of the present disclosure can be applicable to one or more of the foregoing endoscopes.

The present disclosure generally relates to medical devices, and it exemplifies embodiments of an optical probe which may be applicable to an imaging apparatus (e.g., an endoscope. The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

FIG. 1 illustrates an example embodiment of a medical system 1. The medical system 100 (also referred herein as a continuum robot system) comprises a driving unit 310, a bendable medical device 110 (or sheath), a positioning cart 500, an operation console 600, and navigation software 700. The system 100 also interacts with clinical users and external systems (e.g., a computerized tomography (CT) scanner and/or magnetic resonance imaging (MRI) scanner, a fluoroscope, a patient, biopsy tools).

The navigation software 700 and the driving unit 310 are communicatively coupled via a bus, which transmits data between them. Moreover, the navigation software 700 may be coupled to and communicates with a CT scanner or MRI scanner, a fluoroscope, and an image server (not in FIG. 1), which are external of the medical system 100. The image server may be, for example, a DISCOM server that is coupled to a medical imaging device, such as a CT scanner, a MRI scanner, and a fluoroscope. The navigation software 700 processes data provided by the driving unit 2, data provided by images stored on the image server, images from the CT scanner/MRI scanner, and images from the fluoroscope in order to display images on a display device.

The images from the CT scanner/MRI scanner are pre-operatively provided to the navigation software 700. With the navigation software 700, a clinical user can create an anatomical computer model from the images. In some embodiments, the anatomy is a biological lumen such as the lung airway. From the chest images of the CT scanner/MRI scanner, the clinical user can segment the lung airways for clinical use. Thus, a lung-airway map may be created from this data and this lung-airway map may be used to create a planned path. With or without the path, the data can also be used to guide or inform treatments, such as a biopsy using the bendable medical device 110 inserted into the biological lumen.

The driving unit 310 comprises actuators and a control circuitry. The control circuitry is communicatively-coupled with the operation console 600. Also, the driving unit 310 is connected to the bendable medical device 110 so that the actuators in the driving unit 310 operate the medical device 110. Therefore, a clinical user can control the medical device 110 via the driving unit 2. The driving unit 310 is also physically connected to a positioning cart 500. The positioning cart 500 may include one or more positioning arm(s) and a translational stage, and the positioning cart 500 locates the driving unit 310 and the medical device 110 in the intended position against a patient.

The operation console 600, optimally includes one or more displays as well as an input device such as a mouse, joystick, touchscreen, voice activation, or similar.

The medical device may comprise a camera at the distal tip of the medical device (i.e., a 'chip-on-tip design). Alternatively, the medical device will comprise an imaging means for generating an image of the region at the distal tip. For example, the image may be generated via traditional CCD endoscope, a borescope, a fiberscope, or by spectrally encoded endoscopy (see, for example, U.S. Pat. Nos. 7,551, 293; 9,295,391; 10,288,868; and 10,401,610). The medical device will form an image at the distal end of the tip. This image can be used for navigation of the flexible medical device. This image of the interior of the biological lumen or other hollow organ (e.g., a lung) can be combined with the CT, MRI, fluoroscope or other image taken of the area of interest to aid in guidance of the medical device towards a target point.

The medical device 110 may include a tool channel for a biopsy or other interventional tool. Thus, the medical device 110 can guide the biopsy tool to the lesion of the patient. The clinical user can take a biopsy sample from the lesion with the biopsy tool.

Figure 2:
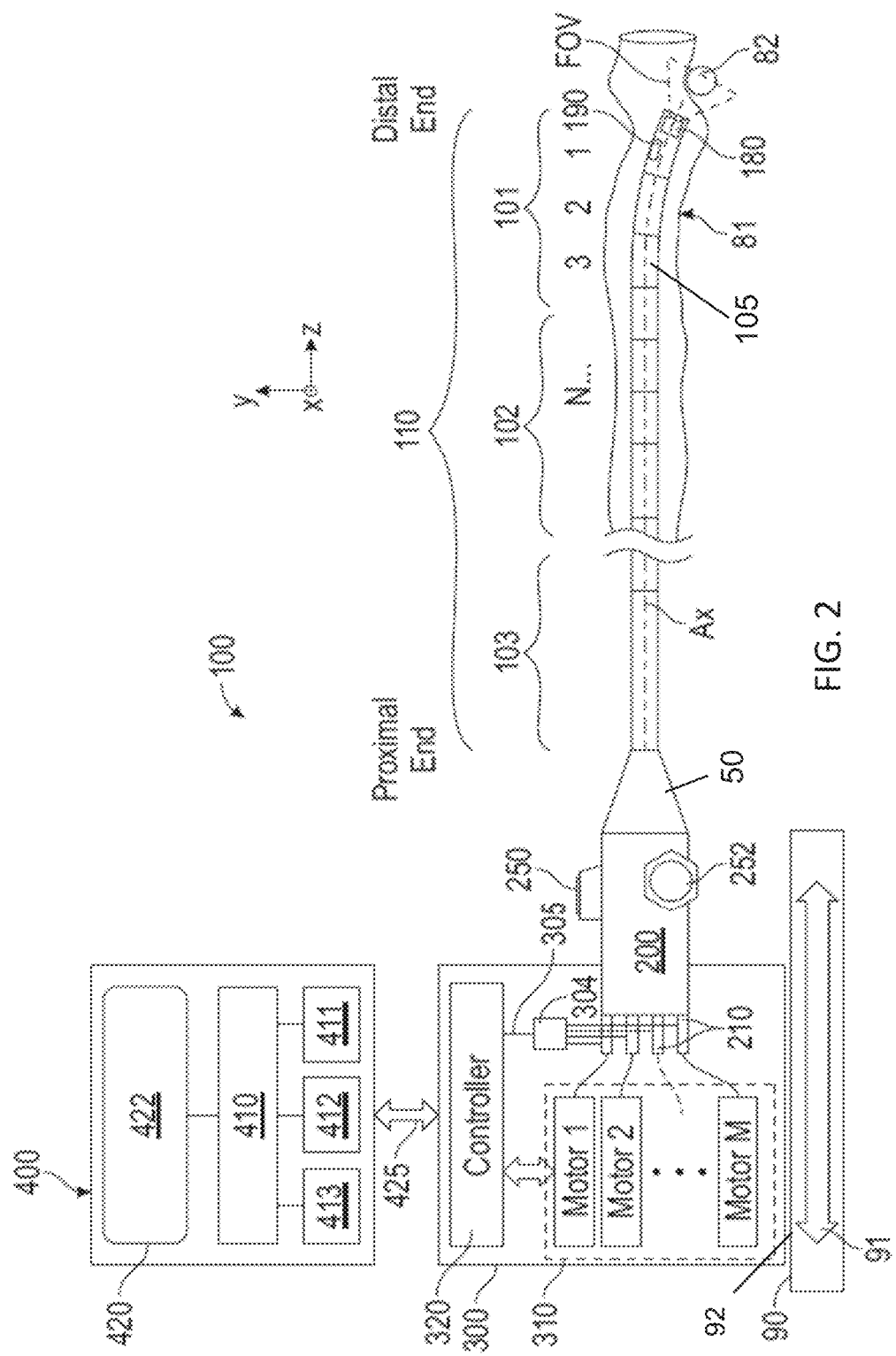
FIG. 2 illustrates an example embodiment of a steerable medical system 100 represented in functional block diagram.

FIG. 2 illustrates a general structure of the steerable medical system 100 in functional block diagram without the user and/or patient. The medical system 100 includes a handle 200 and a bendable medical device 110, which are removably connected to each other by a connector assembly 50. The handle 200 includes an actuator system 300 that is part of the driving unit 310 and which receives electronic commands from computer system 400 to mechanically actuate the bendable medical device 110. The handle 200 is configured to be detachably mounted on the robotic platform 90, which may be part of the positioning cart 500. The robotic platform 90 includes a robotic arm 92 and a stage 91 for robotically guiding the bendable medical device 110 towards a target site within the subject or patient 80. When the handle 200 is not mounted on the robotic platform 90, the handle 200 can be operated manually by the user 10 to control the bendable medical device 110. For treating or examining the patient 80, the steerable medical system 100 may include one or more access ports 250 arranged on or around the handle 200. Access ports 250 can be used for inserting end effectors or for passing fluids to/from the patient. An electromagnetic (EM) field generator 60 interacts with one or more EM sensors 190 arranged on the bendable medical device 110 for tracking the position, shape, and/or orientation of the bendable medical device 110 while being inserted through a bodily lumen 81 towards a target site 82 within the patient 80. The medical device 110 may include a tool channel for a biopsy or other interventional tool. The clinical user can insert and retreat the medical device 110 to perform, for example, a biopsy in the airways of the patient.

During an endoscope procedure, the system processor or CPU 410 of computer system 400 is configured to perform operations based on computer-executable code pre-stored in the system's memory 411. The display screen 420 may include a graphical user interface (GUI) configured to display one or more of patient information 421, an endoscope live-image 422, an intra-operative image 423 (e.g., fluoroscopy), and a pre-operative image 424 (e.g., a slice image) of the patient 80.

The steerable medical system 100 includes a computer system 400 (e.g. a system console), a robotic actuator system 300, and a steerable medical system 100 which is connected to the actuator system 300 via a handle 200. The steerable medical system 100 includes bendable medical device 110 (also described as a steerable sheath) comprised of a proximal section 103, a middle section 102, and a distal section 101 arranged in this order along a longitudinal axis (Ax). The proximal section 103 is a non-steerable section and serves to connect the steerable section to handle 200 and the actuation system. The middle section 102 and the distal section 101 constitute a steerable section of the bendable medical device and are configured to be inserted into a bodily lumen 81 of a patient 80. The steerable distal section 101 (and middle section 102) are divided into multiple bending segments 1, 2, 3 . . . N which are configured to be bent, curved, twisted, and/or rotated when advancing the bendable medical device through intraluminal tortuous paths of a bodily lumen. Each bending segment includes at least one ring-shaped component. By convention, the steerable medical system 100 operates in a three-dimensional (3D) space defined by a 3D coordinate system of x, y, z Cartesian coordinates. The bendable medical device 110 defines at least one tool channel 105 which extends from the proximal end to the distal end along the longitudinal axis Ax. The bendable medical device 110 may include one or more position and/or orientation sensors 190 arranged on the wall the catheter sheath, and may include a removable imaging device 180, such as a fiber camera or a miniature electronic CMOS sensor arranged in the tool channel 105. The imaging device 180 is arranged such that its imaging plane is in the x-y plane, and the longitudinal axis Ax of the bendable medical device 110 extends along the z-axis of the coordinate system.

An example of a bendable medical device 110 and a method of using the medical device via the medical system 100 is described in United States Pat. Pub. No. 2019/0105468, which is incorporated by reference herein in its entirety. Other examples of bendable medical devices and methods of using the medical device via the medical system are disclosed in United States Pat. Pub. Nos. 2018/0243900; 2018/0311006; 2019/0105468; 2019/0015978; and 2019/0105468; and PCT Pub. Nos. WO2018/204202; WO/2020/086749; and WO/2020/092096, all of which are incorporated by reference herein in their entirety.

For inserting an endoscope into a biological lumen 81 such as an airway of a patient 80, the tip (distal end) of the bendable medical device 110 is advanced (navigated) along a center line of the lumen. In this case, an imaging device 180 (e.g., a miniature camera) can be arranged in the tool channel 105 to provide a live-view image of the lumen 81 taken directly from the instrument's field of view (FOV). However, in some embodiments, the bendable medical device 110 may not allow for the arrangement of a camera within the tool channel. In this case, navigation may be provided by intra-procedural guided imaging based on position and/or orientation provided by the one or more sensors 190 arranged along the sheath. In any case, in order to reach a desired target site 82, the bendable medical device 110 must bend, twist and/or rotate in different directions such that the distal section of the bendable medical device continuously changes shape and direction until it reaches an optimal location aligned with target site 82 such as a tumor.

The bending, twisting, and/or rotation (steering) of bendable medical device 110 is controlled by a system comprised of the handle 200, the actuator system 300 and/or the computer system 400. The actuator system 300 includes a micro-controller 320 and an actuator unit 310 which are operatively connected to the computer system 400 via a network connection 425. The computer system 400 includes suitable software, firmware, and peripheral hardware operated by the processor or CPU 410. The computer system 400, the actuator system 300, and the handle 200 are operably connected to each other by the network connection 425 (e.g., a cable bundle or wireless link). In addition, the computer system 400, the actuator system 300 and the handle 200 are operatively connected to each other by the robot platform 90, which may include one or more robotic arms 92 and translation stage 91, which is also incorporated in the driving unit 310. In some embodiments, the actuator system 300 may include or be connected to a handheld controller, such as a gamepad controller or a portable computing device like a smart phone or a tablet. Among other functions, the computer system 400 and actuator system 300 can provide a surgeon or other operator with a graphical user interface (GUI) and patient information shown in the display screen 420 to operate the steerable medical system 100 according to its application.

Figure 3:
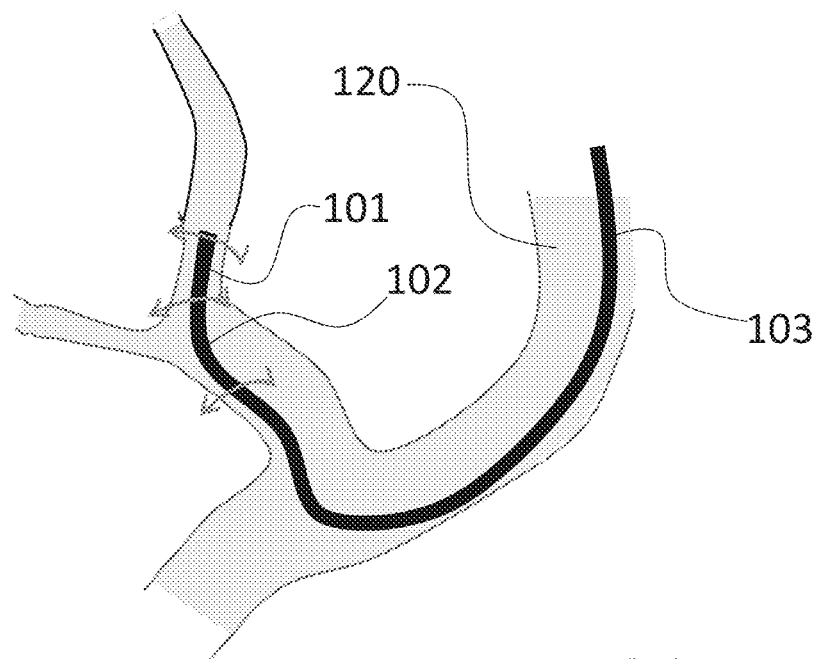
FIG. 3 illustrates a lung with a pathway for endoscope insertion.

FIG. 3 illustrates the bendable medical device having three sections (101, 102, and 103) situation in a body lumen, which can be the lung 120. As indicated by the lung 120, at each bifurcation, the airway may become smaller such that the bendable medical device can no longer fit into the airway.

Figure 4:
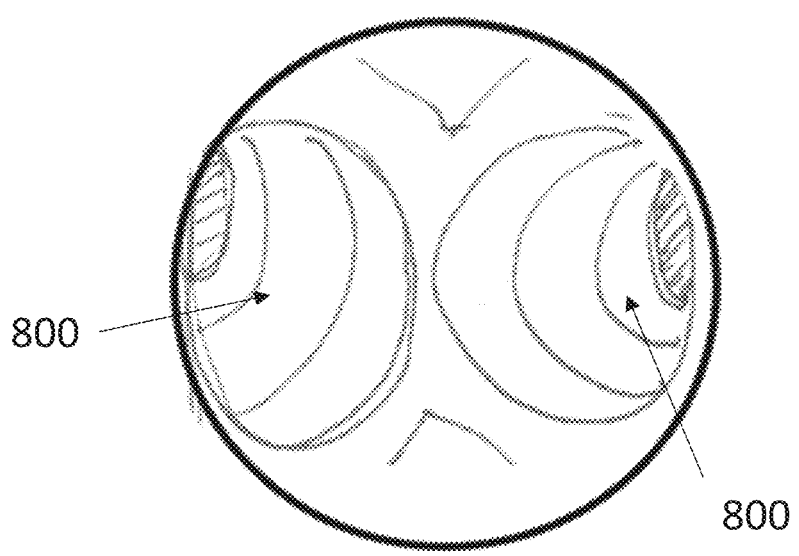
FIG. 4 illustrates an endoscope view of an airway structure without an overlay.

FIG. 4 shows an example endoscope view of airway structures 800 of a patient. This is a general image and has no information as to how the bendable medical device will fit or move through the airway. This view is what the clinical user can use to navigate through the lung. This view may be combined with CT or MRI imaging or fluoroscopy imaging of the lung to aid in the navigation for a medical procedure.

Figure 5:
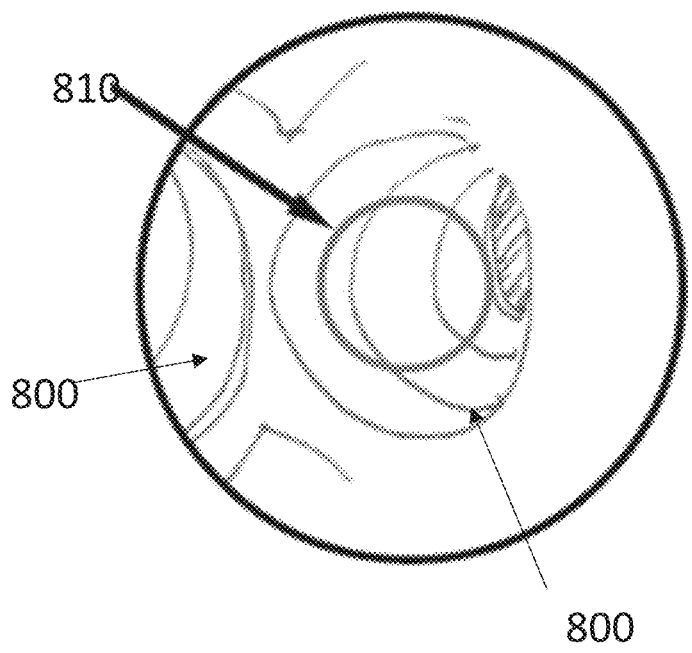
FIG. 5 illustrates an endoscope view of an airway structure with an overlay in accordance with an example embodiment.

FIG. 5 shows the same endoscope view of FIG. 4, but with an overlay 810 (a first overlay) representing the outer diameter of the medical device 110, which can be displayed on the operation console 600 during a procedure. The overlay 810 depicts a representation of the outer diameter of the medical device 110 appropriately scaled to a focal plane of the airway structures 800 shown in the endoscope view. The airway structures 800 can be shown as a computer generated virtual bronchoscope or a live bronchoscope view.

The appropriate size of the overlay, which relates the outer diameter of the medical device 11 to the imaged lumen size can be determined by analyzing the airway structures 810 reconstructed from CT data/MRI data that is already obtained by the system. That is, in order for system 100 to plan a path to the target region, CT data/MRI data is imported into the navigation software 700, which then reconstructs the airway structures 800 digitally. Accordingly, using this same data, the diameter of the airway structures 800 can be calculated at any given focal plane position using the CT data/MRI data.

Because the medical device 110 outer diameter is fixed, a representative image (i.e., the overlay 810 representing the outer diameter of the medical device 110) can be provided for any given focal plane in front of the medical device 110 as it travels through a pathway.

The focal plane for the overlay may be set as a predetermine distance in front of the medical device 110, such as 0 mm, 15 mm, etc. In other embodiments, the focal plane is determined via user testing. As such, the focal plane may be a pre-determined value. In other embodiments, the focal plane may set as the measured or estimated distance between the front of the medical device 110 and the tissue structure located in front of the camera. This measured or estimated distance may be determined, for example, by an ultra-low powered laser at the distal tip of the medical device, where the laser, like range finder, can be used to measure the distance.

Figure 6:
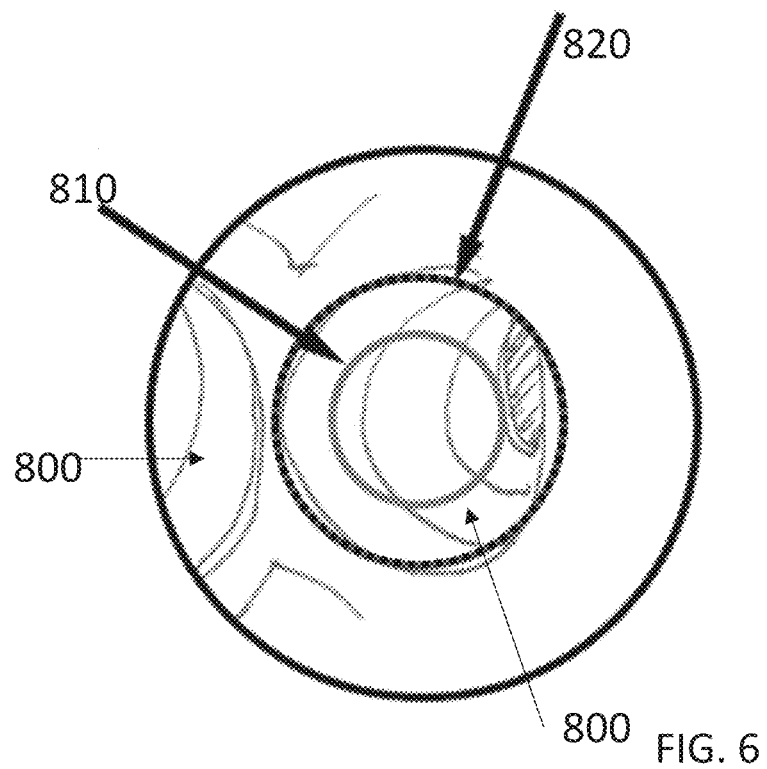
FIG. 6 illustrates an endoscope view of an airway structure with multiple overlays in accordance with an example embodiment.

FIG. 6 shows the same endoscope view of FIG. 4, in accordance with another aspect of the disclosure. In particular, FIG. 6 shows another aspect where in addition to the overlay 810 representing the outer diameter of the medical device 110, another overlay 820 (a second overlay) representing a diameter of the airway structure 800 is also shown. The overlay 820 representing a diameter of the airway structure 800 may be, for example, a best-fit circle provided on the calculated airway diameter for a given focal plane. The aspect shown in FIG. 6 may similarly be displayed on the operation console 600 during the procedure. In this embodiment, the overlay 810 is exemplified in this figure as a solid circle. In some embodiments, the overlay 810 may be of a specific color or type (e.g., dotted or dashed) for clarity. For example, the second overlay 820 as shown in FIG. 6 is shown is a dashed line. In some embodiments, the two overlay may be the same or distinguished by a different combination of color and/or type.

During the procedure as the medical device 110 travels through the patient, the system can be configured to provide a warning/feedback to the operator under certain conditions. For example, as the diameters of the airway structure 800 and the outer diameter of the medical device 110 approach each other, the system may issue a warning to the operator via the operation console 600. For example, the notification may be an audible alarm, a tactile change/alarm, and/or a visual alarm. The visual alarm may include flashing warning symbols/text or any other change in display such as a color change, a pattern change, a change in the thickness of the overlay lines, etc. In another aspect, as the diameter of the airway structure 800 and the outer diameter of the medical device 110 approach each other, the system may issue haptic feedback to the operator.

For example, in a case that the diameter of the outer diameter of the medical device 110 is as large as (or approaches in size) to the diameter of the airway structure 10, and when the operator is operating the system using an input device (e.g., a joystick), the system may provide haptic feedback via the operating device when the medical device no is within a predetermined distance from reaching a point in the airway where the diameter of the airway structure 800 is the same size or, alternatively, a similar size, to the medical device no. The intensity of the haptic feedback may be increased as the operator continues to actuate the operating device to move the medical device progressively closer to the diameter of the airway structure. For example, the haptic feedback may make it more difficult for the operator to actuate the operating device to continue to move the medical device toward the diameter of the airway structure. That is, the haptic feedback may be a force that resists further actuation of the operating device by the operator, where the force resisting the actuation progressively increases as the medical device 110 approaches the diameter of the airway structure. In other words, it becomes progressively more difficult for the operator to actuate the operating device in a manner that that moves the medical device 110 closer to the diameter of the airway structure 10.

In another example, in a case that the diameter of the outer diameter of the medical device 110 is as large as (or approaches in size to) the diameter of the airway structure 10, the overlay 810 will change the displayed color, pattern, thickness, or some other visual indication will be provided.

This feedback (e.g., haptic, visual, or alternatively via some other visual or auditory means) can be provided when the outer diameter of the medical device is the same size as the diameter of the airway structure at the focal plane. To give the clinical user additional time to indicate the tightness in fit within the airway, the feedback may occur when the outer diameter of the medical device is near but not yet the same diameter as the airway (e.g., 80% or 90%). Alternatively, since the airway is relatively flexible and will expand, the feedback may be given only after the medical device diameter measure larger than the nominal airway diameter.

Figure 7:
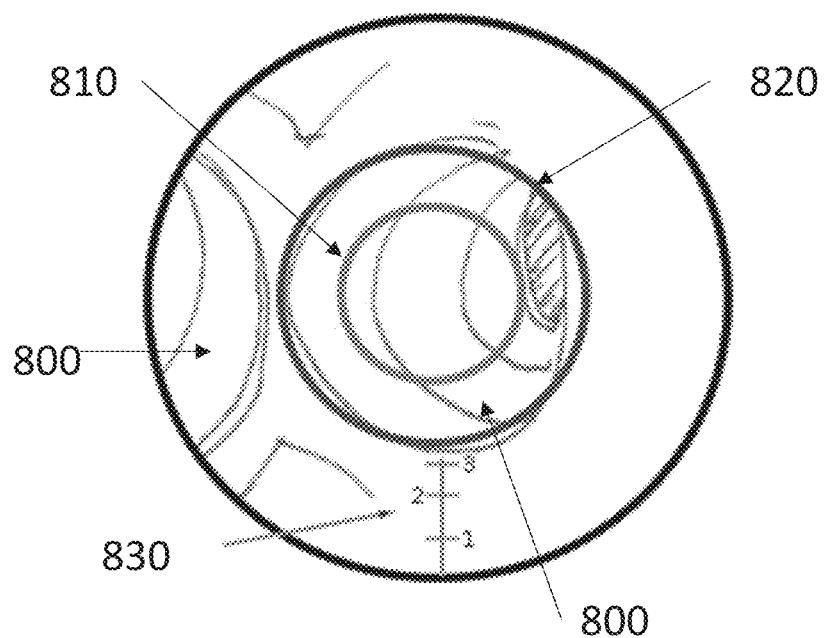
FIG. 7 illustrates an endoscope view of an airway structure with multiple overlays in accordance with another example embodiment.

FIG. 7 shows an endoscope view, in accordance with another aspect of the disclosure. In particular, FIG. 7 shows another aspect where in addition to the overlay 810 representing the outer diameter of the medical device 110, and the overlay 820 representing a diameter of the airway structure 10, a distance indicator 830 is further provided. The distance indicator 830 may be a number scale representing the distance from the tip of the medical device 110 to the focal plane of the projected overlay 810 representing the outer diameter of the medical device 110 and/or the other overlay 820 representing a diameter of the airway structure 10. The aspect shown in FIG. 7 may be displayed on the operation console 600 during the procedure, either as an additional display or as an alternative to the indicator in the endoscopic view.

Figure 8:
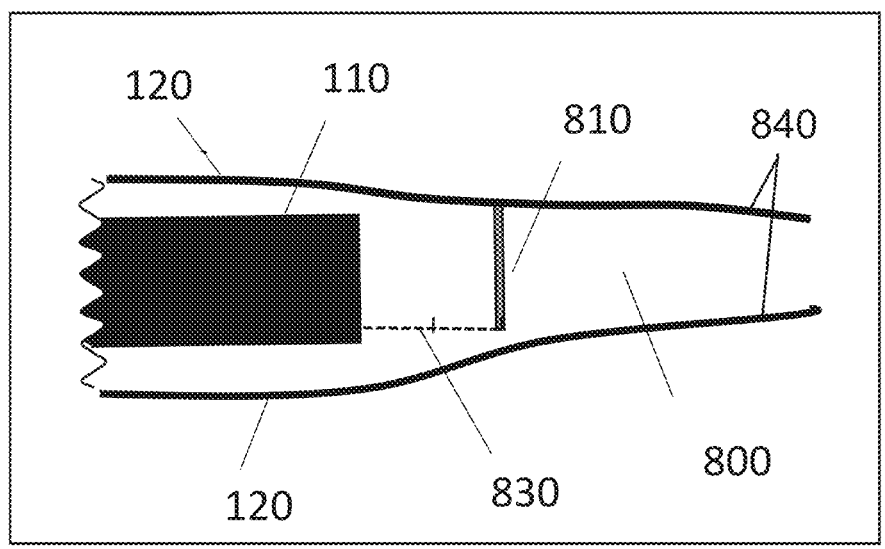
FIG. 8 illustrate a side view of an airway structure with multiple overlays in accordance with another example embodiment.

FIG. 8 shows a side view of the airway structure 800 that may also or alternatively be displayed to the user in another aspect of the present disclosure. In particular, the side view of FIG. 8 shows the medical device 110 in the process of traveling through an airway structure 10, where both airway walls 840 are shown. In the side view of FIG. 8, the overlay 810 representing the outer diameter of the medical device is projected similar to FIGS. 4-7. However, because FIG. 8 is a side view, the overlay 810 representing the outer dimeter of the medical device appears as a line. In the side view of FIG. 8, the distance indicator 830 is also provided. Because FIG. 8 is a side view, the relative length of distance indicator 830 is more immediately apparent as compared to the endoscope view of FIGS. 5-7. The aspect shown in FIG. 8 may similarly be displayed on the operation console 600 during the procedure.

In an aspect of the present disclosure, the system 100 may provide one or more or all of the views of FIGS. 4 to 8 to the operator. In another aspect, the system 100 may be configured so that the user may select which views to display.

The system 100 may be regulated, controlled, and/or directed by one or more processors in communication with the controller and optionally other components and/or subsystems of the overall system 1. The processor may operate based on instructions in a computer readable program stored in a non-transitory computer readable memory. The processor may be or include one or more of a CPU, MPU, GPU, ASIC, FPGA, DSP, and a general purpose computer. The processor may be a purpose built controller or may be a general purpose computing device that is adapted to be a controller. Examples of a non-transitory computer readable memory include but are not limited to RAM, ROM, CD, DVD, Blu-Ray, hard drive, networked attached storage (NAS), an intranet connected non-transitory computer readable storage device, and an internet connected non-transitory computer readable storage device.

e. Embodiment(s) of the present disclosure can be realized by computer system 400 or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer system may comprise one or more processors (e.g., central processing unit (CPU) 410, micro processing unit (MPU)) and may include a network of separate computers or separate processors to read out and execute the computer executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. For example, the present disclosure has been described above in terms of exemplary embodiments. However, there are many variations not specifically described to which the present disclosure could be applicable. For example, while the various embodiments are described with respect to an endoscope for use in medical procedures, the disclosure would be also applicable with respect to mechanical procedures of a borescope for use within various mechanical structures. Therefore, the scope of the following claims is to be accorded the broadest interpretation so as to encompass all such modifications and equivalent structures and functions.

The invention claimed is:

1. A medical system comprising:
a medical device having an outer diameter and a distal tip;
a display device; and
a controller configured to:
acquire data regarding a biological lumen;
acquire an image of the biological lumen from the distal tip of the medical device;
generate an overlay representing the outer diameter of the medical device;
generate an overlay representing a diameter of the biological lumen;
display, on the display device, the overlay representing the outer diameter of the medical device and the overlay representing the diameter of the biological lumen on the acquired image of the biological lumen, wherein both overlays are displayed at a focal plane of the biological lumen.

2. The medical system of claim 1, wherein the overlay representing the diameter at the focal plane of the biological lumen is a best-fit circle calculated from the acquired data.

3. The medical system of claim 1, wherein the biological lumen is an airway structure having the diameter.

4. The medical system of claim 3, wherein the controller is further configured to provide a warning when the outer diameter of the medical device is larger than the diameter of the airway structure at the focal plane of the airway structure.

5. The medical system of claim 4, wherein the warning is selected from a group consisting of an audible alarm, a tactile alarm, and a visual alarm.

6. The medical system of claim 5, wherein the visual alarm is a flashing warning or a change in a display color, a change in display pattern, or a change in a thickness of the overlay representing the outer diameter of the medical device.

7. The medical system of claim 1, wherein the controller is further configured to generate a scale indicating a distance from an end of the medical device to the focal plane of the biological lumen.

8. The medical system of claim 7, wherein the controller is further configured to display, on the display device, the scale indicating the distance from the end of the medical device to the focal plane of the biological lumen.

9. The medical system of claim 1, wherein the acquired data is computerized tomography (CT) scanner data and/or magnetic resonance imaging (MRI) scanner data.

10. The medical system of claim 1, wherein the controller is configured to acquire the image of the biological lumen by receiving an optical image.

11. The medical system of claim 1, wherein the controller is configured to acquire the image of the biological lumen by reconstructing the image based on the acquired data.

12. The medical system of claim 1, wherein the controller further comprises an actuator system for steering the medical device.

13. The medical system of claim 1, wherein the controller is further configured to provide haptic feedback to an operator when the outer diameter of medical device reaches a predetermined size compared to the diameter of the biological lumen at the focal plane.

14. The medical system of claim 13, wherein an intensity of the haptic feedback progressively increases as the outer diameter of the medical device approaches the diameter of the biological lumen at the focal plane.

15. The medical system of claim 14, wherein the haptic feedback is a resistive force that resists an action by the operator to instruct the controller to move the medical device within the biological lumen.

16. A method for controlling a display, the method comprising:
acquiring data about a size and/or a shape of a biological lumen;

displaying an image of the biological lumen obtained from a medical device inserted in the biological lumen;

generating an overlay representing an outer diameter of the medical device; and displaying, on a display device, the overlay representing the outer diameter of the medical device and an overlay representing a diameter of the biological lumen on the image of the biological lumen, wherein both overlays are displayed at a focal plane of the biological lumen.

17. The method of claim 16, further comprising steering the medical device in the biological lumen using an actuator system.

* * * * *